(12) United States Patent
Sriram et al.

(10) Patent No.: US 7,773,217 B2
(45) Date of Patent: Aug. 10, 2010

(54) PROBE FOR TUNABLE LASER RAMAN SPECTROSCOPY SYSTEM

(75) Inventors: Tirunelveli S. Sriram, Acton, MA (US);
David A. Coppeta, Atkinson, NH (US);
James Zambuto, Winchester, MA (US)

(73) Assignee: Axsun Technologies, Inc., Billerica, MA (US)

( * ) Notice: Subject to any disclaimer, the term of this patent is extended or adjusted under 35 U.S.C. 154(b) by 929 days.

(21) Appl. No.: 11/357,899

(22) Filed: Feb. 17, 2006

(65) Prior Publication Data
US 2007/0195320 A1 Aug. 23, 2007

(51) Int. Cl.
*G01J 3/44* (2006.01)

(52) U.S. Cl. ................................ 356/301; 356/326

(58) Field of Classification Search .............. 356/301, 356/307
See application file for complete search history.

(56) References Cited

U.S. PATENT DOCUMENTS

| | | | |
|---|---|---|---|
| 4,919,535 A | 4/1990 | Hohberg et al. | |
| 5,112,127 A | 5/1992 | Carrabba et al. | |
| 5,194,912 A | 3/1993 | Batchelder et al. | |
| 5,377,004 A | 12/1994 | Owen et al. | |
| 5,442,438 A | 8/1995 | Batchelder et al. | |
| 5,657,120 A | 8/1997 | Smith | |
| 5,689,333 A | 11/1997 | Batchelder et al. | |
| 5,862,273 A | 1/1999 | Pelletier | |
| 5,943,128 A | 8/1999 | Slater | |
| 5,946,090 A | 8/1999 | Tashiro et al. | |
| 5,956,138 A | 9/1999 | Slater | |
| 5,974,211 A | 10/1999 | Slater | |
| 6,038,363 A | 3/2000 | Slater et al. | |
| 6,310,686 B1 | 10/2001 | Jiang | |
| 6,351,306 B1 | 2/2002 | Tedesco et al. | |
| 6,442,736 B1 | 8/2002 | Girard et al. | |
| 6,483,581 B1 | 11/2002 | Ben-Amotz et al. | |
| 6,563,854 B2 | 5/2003 | Tedesco | |
| 6,583,873 B1 * | 6/2003 | Goncharov et al. | 356/326 |
| 6,603,545 B2 | 8/2003 | Slater | |
| 6,621,574 B1 | 9/2003 | Forney et al. | |

(Continued)

FOREIGN PATENT DOCUMENTS

WO    WO 03/078945 A1    9/2003

(Continued)

OTHER PUBLICATIONS

Eckenrode, Brian A., et al, "Portable Raman Spectroscopy Systems for Field Analysis," Forensic Science Communications, vol. 3, No. 4, Oct. 2001, 18 pp.

(Continued)

*Primary Examiner*—Tarifur Chowdury
*Assistant Examiner*—Tara S Pajoohi
(74) *Attorney, Agent, or Firm*—Houston Eliseeva LLP

(57) ABSTRACT

A probe of a Raman spectroscopy system has a wavelength and/or amplitude referencing system for determining a wavelength of the excitation signal. Preferably, this referencing system is near an output aperture, through which the excitation signal is transmitted to the sample. In this way, any birefringence or polarization dependent loss (PDL) that may be introduced by optical elements in the system can be compensated for since the wavelength reference system will detect the effect or impact of these elements.

18 Claims, 3 Drawing Sheets

U.S. PATENT DOCUMENTS

| | | |
|---|---|---|
| 6,650,412 B1 | 11/2003 | Slater |
| 6,657,724 B1 | 12/2003 | Dunstan et al. |
| 6,757,060 B2 | 6/2004 | Davis et al. |
| 6,809,812 B2 | 10/2004 | Yin |
| 6,809,813 B2 | 10/2004 | Bennett et al. |
| 6,873,409 B1 | 3/2005 | Slater |
| 6,885,445 B2 | 4/2005 | Bennett et al. |
| 6,897,951 B2 | 5/2005 | Womble et al. |
| 6,907,149 B2 | 6/2005 | Slater |
| 7,403,281 B2 * | 7/2008 | Carron et al. ............... 356/301 |
| 2003/0168735 A1 * | 9/2003 | Ohsumi ..................... 257/734 |
| 2004/0004194 A1 * | 1/2004 | Amblard et al. .......... 250/458.1 |
| 2005/0007583 A1 | 1/2005 | DiFoggio |
| 2005/0168735 A1 * | 8/2005 | Boppart et al. .............. 356/301 |
| 2005/0264808 A1 | 12/2005 | Wang |

FOREIGN PATENT DOCUMENTS

WO    WO 2005/060622 A2    7/2005

OTHER PUBLICATIONS

"Guide to Raman Instrumentation," InPhotonics: Criteria for choosing a Raman spectrometer, May 2005, 2 pp.

* cited by examiner

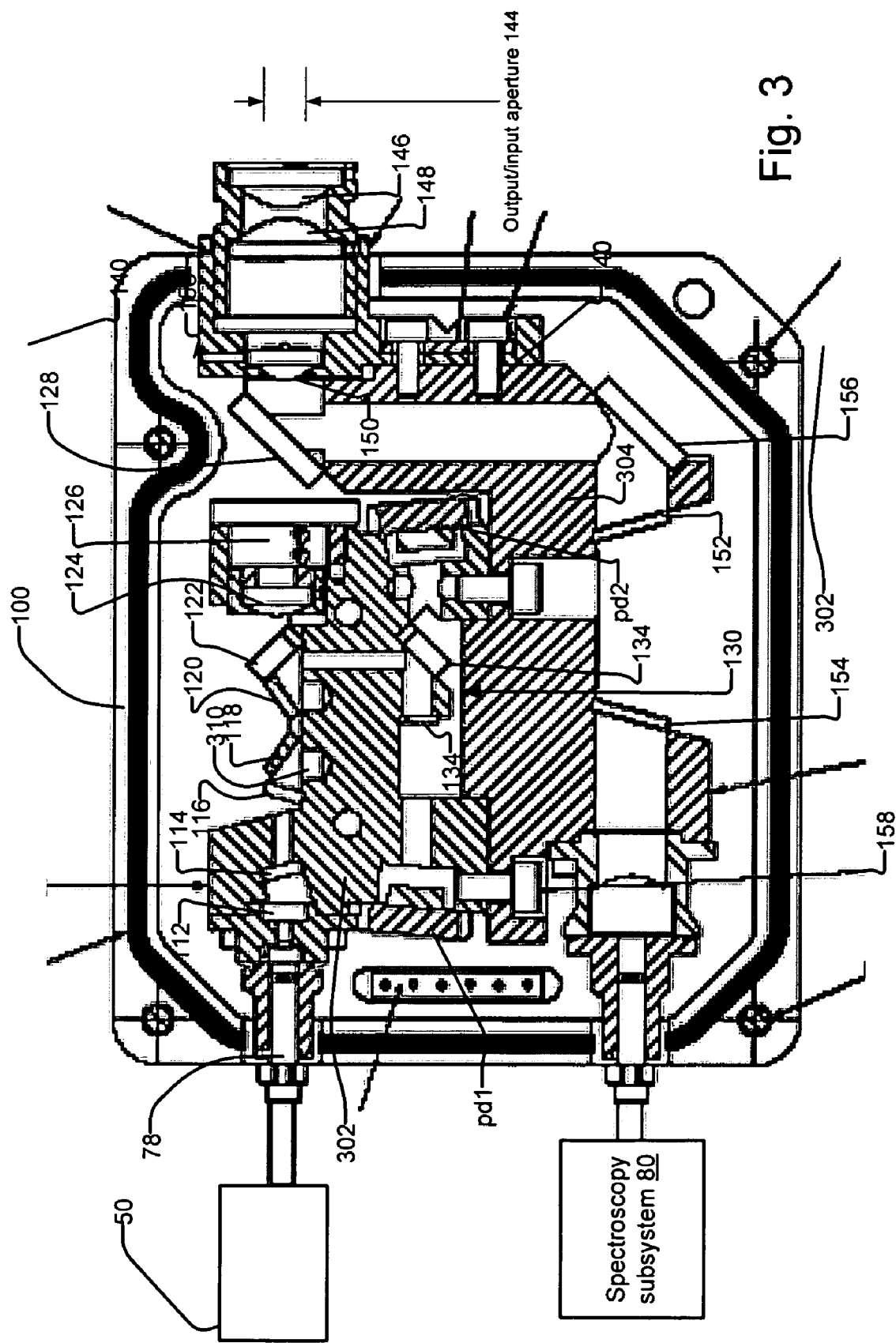

PROBE FOR TUNABLE LASER RAMAN SPECTROSCOPY SYSTEM

BACKGROUND OF THE INVENTION

Raman spectroscopy is similar to infrared (IR), including near infrared (NIR), spectroscopy but has several advantages. The Raman effect is highly sensitive to slight differences in chemical composition and crystallographic structure. These characteristics make it very useful for substance identification such as the investigation of illegal drugs as it enables distinguishing between legal and illicit compounds, even when the compounds have a similar elemental composition. In other applications, taggants, with known Raman signatures, are used as markers for goods.

Raman spectroscopy has additional advantages. When using IR spectroscopy on aqueous samples, a large proportion of the vibrational spectrum can be masked by the intense water signal. In contrast, with Raman spectroscopy, aqueous samples can be more readily analyzed since the Raman signature from water is relatively weak. Also, because of the poor water signature, Raman spectroscopy is often useful when analyzing biological and inorganic systems, and in studies dealing with water pollution problems.

Raman scattering may be regarded as an inelastic collision of an incident photon with a molecule. The photon may be scattered elastically, that is without any change in its wavelength, and this is known as Rayleigh scattering. Conversely the photon may be scattered inelastically resulting in the Raman effect.

There are two types of Raman transitions. Upon collision with a molecule, a photon may lose some of its energy. This is known as Stokes radiation. Or, the photon may gain some energy—this is known as anti-Stokes radiation. This happens when the incident photon is scattered by a vibrationally excited molecule—there is gain in energy and the scattered photon has a higher frequency or shorter wavelength.

When viewed with a spectrometer, both the Stokes and anti-Stokes radiation are composed of lines that correspond to molecular vibrations of the substance under investigation. Each compound has its own unique Raman spectrum, which can be used as a fingerprint for identification.

The Raman process is nonlinear. When incident photons have a low intensity, only spontaneous Raman scattering will occur. As the intensity of the incident light wave is increased, an enhancement of the scattered Raman field can occur in which initially scattered Stokes photons can promote further scattering of additional incident photons. With this process, the Stokes field grows exponentially and is known as stimulated Raman scattering (SRS).

One disadvantage associated with Raman spectroscopy, however, is fluorescence from the sample or impurities in the sample. In many cases, the fluorescence response can overwhelm the typically much weaker Raman signature. This can make detection of small peaks in the Raman signature difficult. Often, fluorescence can be mitigated by moving to a longer wavelength excitation. This can create other problems, however.

One robust solution to the fluorescence response is using excitation signals at multiple wavelengths. Specifically, in the past others have suggested to use excitation signals that comprise two excitation wavelengths, generated by two different single frequency lasers. This is sometimes referred to as Shifted Excitation Raman Difference Spectroscopy (SERDS). Then, by looking at the spectrums generated by each of the wavelengths, the fluorescence signal can be identified since it changes very little with excitation wavelength, whereas the Raman signal changes as a direct function of the excitation wavelength. In the simplest example, the spectra at two excitation wavelengths are subtracted to remove the highly stationary fluorescence response. Recently, this solution has been further enhanced by using a continuously tunable semiconductor diode laser system. In these systems, the spectral response of the sample is monitored as the excitation signals wavelength is scanned over a scan range. By looking at how the spectral response changes with the tuning of the excitation signal and how it does not change, the Raman response can be separated from the fluorescence response of the sample.

SUMMARY OF THE INVENTION

The use of a tunable laser excitation signal, however, creates other problems. Specifically, in older single frequency systems, or dual frequency systems, the wavelength of the excitation signal was static or drifted only by a small amount due to ambient temperature changes. In contrast, with the newer tunable laser systems, the instantaneous wavelength of the excitation signal must be compared to the instantaneous spectral response from the sample as the excitation source is tuned through the scan range. Moreover, it is often important to know the instantaneous power of excitation signal.

Similar these problems have been confronted by providing some sort of wavelength and/or power monitoring in the tunable laser system. In tunable Raman systems, the accurate detection of the instantaneous wavelength and/or amplitude of the tunable excitation signal is made complex by the inherent, differing optical characteristics of optical elements at different wavelengths. One example is the changing birefringence as a function of wavelength in the optical elements. A further issue concerns polarization. In these newer tunable laser excitation source systems, semiconductor diode lasers are used to generate the excitation signal. This class of lasers, however, produces highly polarized light, generating light along only one axis of the device. This can give rise to polarization dependent loss (PDL) due to changes in polarization or how the polarization is changed at different wavelengths of the excitation signal as it is tuned across the scan range and in different ambient environments.

The present invention is directed to a probe of a Raman spectroscopy system. It has a wavelength and/or amplitude reference system for determining a wavelength and/or amplitude of the excitation signal. Preferably, this wavelength reference system is near an output aperture, through which the excitation signal is transmitted to the sample. In this way, any birefringence or PDL that may be introduced by optical elements in the system can be compensated for since the wavelength reference system will detect the effect or impact of these elements. Moreover, in the preferred embodiment, both the wavelength and the amplitude of the excitation signal are detected.

In general, according to one aspect, the invention features a probe subsystem for a Raman spectroscopy system. This probe subsystem comprises a wavelength reference system for determining a wavelength of an excitation signal and an output aperture through which the excitation signal is transmitted to the sample.

In the preferred embodiment, the wavelength reference system comprises at least one reference detector. In the preferred embodiment, a first reference detector and a second reference detector are used. A wavelength reference element filters the excitation signal received by the wavelength reference detector or detectors. This wavelength reference renders the response at the reference detector dependent upon the wavelength of the excitation signal, allowing a controller, for example, to determine the instantaneous wavelength of the excitation signal.

In specific embodiments, a partially reflective mirror is placed in a path of the excitation signal to tap a portion of the excitation signal received by the wavelength reference system. Excitation optical elements are also preferably provided for shaping a beam of the excitation signal after detection of a portion of the excitation signal by the wavelength reference system. In a preferred embodiment, separation optics is used for enabling transmission of the excitation beam to the sample and receipt of the spectroscopic response from the sample along a common axis through a common aperture. A separation system comprising a mirror with a hole or optical port of the excitation signal is preferably used.

In the preferred embodiment, the probe subsystem receives the excitation signal from a semiconductor tunable laser subsystem. Specifically, the excitation signal is generated by one or more semiconductor diode lasers. The excitation signal is transmitted from these diode lasers to the probe subsystem through an optical fiber. Preferably, polarization-controlling system such as polarization-maintaining fiber is used to provide polarization control such that the polarization is stable in spite of any mechanical shock or other perturbations to the system. To further address polarization issues, one or more polarizers are preferably provided in the probe subsystem. Typically, these are free space optical elements that improve the polarization of the beam transmitted through the probe subsystem. Further, at least one amplified spontaneous emission filter is provided for attenuating amplified spontaneous emission in the excitation signal after receipt from the optical fiber.

In general, according to another aspect, the invention features a Raman spectroscopy system. This system comprises a tunable laser excitation subsystem comprising at least one tunable semiconductor diode for generating an excitation signal. A probe subsystem is also provided comprising a wavelength reference for determining a wavelength of the excitation signal and an output aperture through which the excitation signal is transmitted to the sample. A spectrometer subsystem is provided for resolving a spectrum of light returning from the sample. A controller then determines a Raman spectral response of the sample in response to the spectrum of light resolved by the spectrometer subsystem and the wavelength of the excitation signal from the wavelength reference system.

In general, according to another aspect, the invention features a spectroscopy method. This method comprises generating an excitation signal having a varying wavelength within a scan range. This excitation signal is transmitted to a probe. In the probe, the wavelength and/or amplitude of the excitation signal is determined, and then the excitation signal is transmitted from the probe to the sample. Light is detected from the sample. A Raman spectral response of the sample is determined in response to the detected light from the sample and the wavelength and amplitude of the excitation signal.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 3 is a plan, scale view of the probe subsystem according to the present invention.

DETAILED DESCRIPTION OF THE PREFERRED EMBODIMENTS

Figure 1:
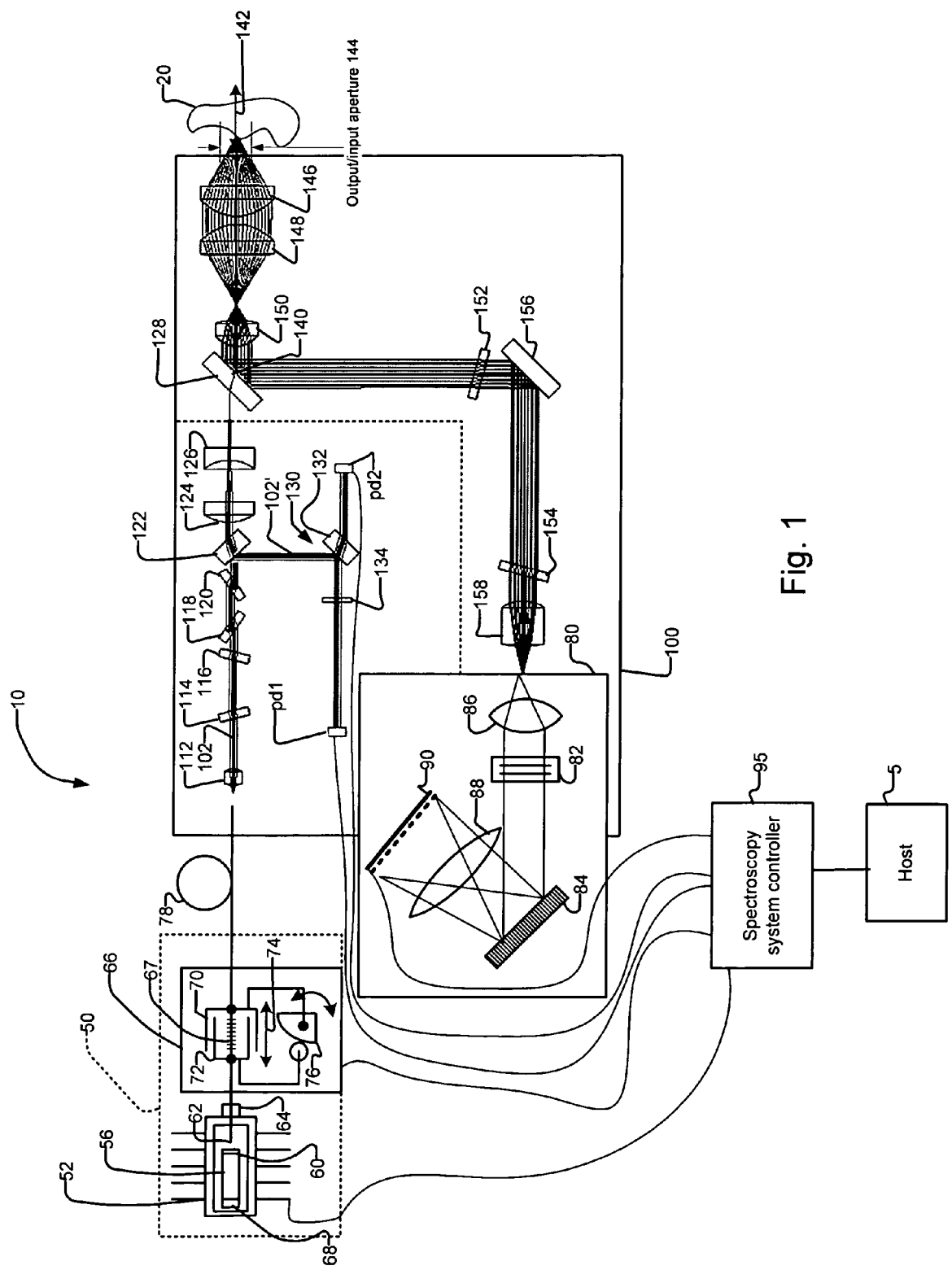
FIG. 1 is a schematic view showing a Raman spectroscopy system according to the present invention comprising a semiconductor tunable laser subsystem, the inventive Raman probe subsystem, and a spectroscopy subsystem.

FIG. 1 shows a Raman spectroscopy system 10, which has been constructed according to the principles of the present invention.

Specifically, it comprises a semiconductor tunable laser subsystem 50. The tunable laser subsystem 50 comprises a semiconductor diode module 52. In the illustrated example, this module 52 is a hermetic package such as a butterfly hermetic package. The diode laser module 52 holds a semiconductor gain element 56. In the present embodiment, this gain element 56 is a semiconductor optical amplifier, and specifically, a reflective semiconductor optical amplifier. These semiconductor reflective optical amplifiers 56 comprise a reflective back facet 68 and an antireflection coated (AR) coated front facet 60. They are useful in the construction of external cavity tunable semiconductor lasers.

In the illustrated embodiment, the external cavity tunable laser configuration provided by a wavelength tunable element module 66, which provides tunable narrow band feedback into the semiconductor gain element 56. In the preferred embodiment, this is a Bragg grating tuning system. Specifically, it comprises a fiber Bragg grating 67 that is mechanically stretched by a stretcher system. Specifically, a first half of the stretcher 70 and a second half of the stretcher 72 are moved toward and away from each other in the direction of arrow 74. In the current embodiment, a cam system 76 is used in order to mechanically stretch the fiber Bragg grating 67.

An optical fiber pigtail 78 transmits the excitation signal from the semiconductor tunable laser subsystem 50 to the probe subsystem 100. In the preferred embodiment, the fiber pigtail 78 is polarization controlling fiber that controls the polarization of the light transmitted through it. Specifically, polarization controlling fiber is used between the gain element 56 and the grating 67 and between the grating and the probe subsystem 100. In the preferred embodiment, it is polarization maintaining fiber, although other polarization controlling systems could be used such as polarization stripping systems or polarizing fiber.

The light from the semiconductor chip 56 is coupled into a fiber pigtail 78 via a facet 62. This fiber goes through the hermetic package 52 via a fiber feedthrough 64 in one example.

The probe subsystem 100 comprises a first collimating lens 112. This receives the excitation signal from the fiber pigtail 78 and forms a collimated beam from the typically diverging beam that exits the fiber 78. The excitation signal 102 is preferably filtered to remove amplified spontaneous emission—a spectrally continuous emission from the semiconductor laser that is broadband in spectrum. In the preferred embodiment, two spectral notch or bandpass filters are provided as spontaneous emission filters 114 and 116. These suppress the ASE emission by reflecting any light that is outside the scan range of the excitation signal 102.

The probe subsystem 100 also preferably provides for polarization filtering of the excitation signal 102. In a preferred embodiment, two polarizers 118 and 120 are used. These filters 118, 120 ensure that the excitation signal 102 has substantially only a single polarization. The single polarization of the excitation signal is important because of polarization dependent loss (PDL) in the taps and other polarization changes due to ambient changes, for example, that lead to tracking errors of the wavelength and/or amplitude of the excitation signal 102 that can not be effectively addressed with calibration.

A partially reflective excitation mirror 122 is provided in the path of the excitation signal 102. This reflects a portion 102' of the excitation signal to a wavelength/amplitude reference system 130.

The wavelength/amplitude reference system 130 in the preferred embodiment detects both the instantaneous wavelength of the excitation signal 102 along with its amplitude or power. In the current implementation, this is achieved by using a partially reflective reference mirror 132. This reflects the excitation signal received by the wavelength reference system 130 through a wavelength reference element 134. In the preferred embodiment, this is a fixed wavelength Fabry Perot Etalon. A slope filter could also be used. As such, the reference has an Airy transmission function to pass light at specific wavelengths and reflect wavelengths outside those ranges. The light transmitted through the wavelength reference element 134 is detected by a first photodetector pd1. Light reflected by the wavelength element 134 is transmitted back through the partially reflective reference mirror 132 to a second photodiode pd2.

Figure 2:
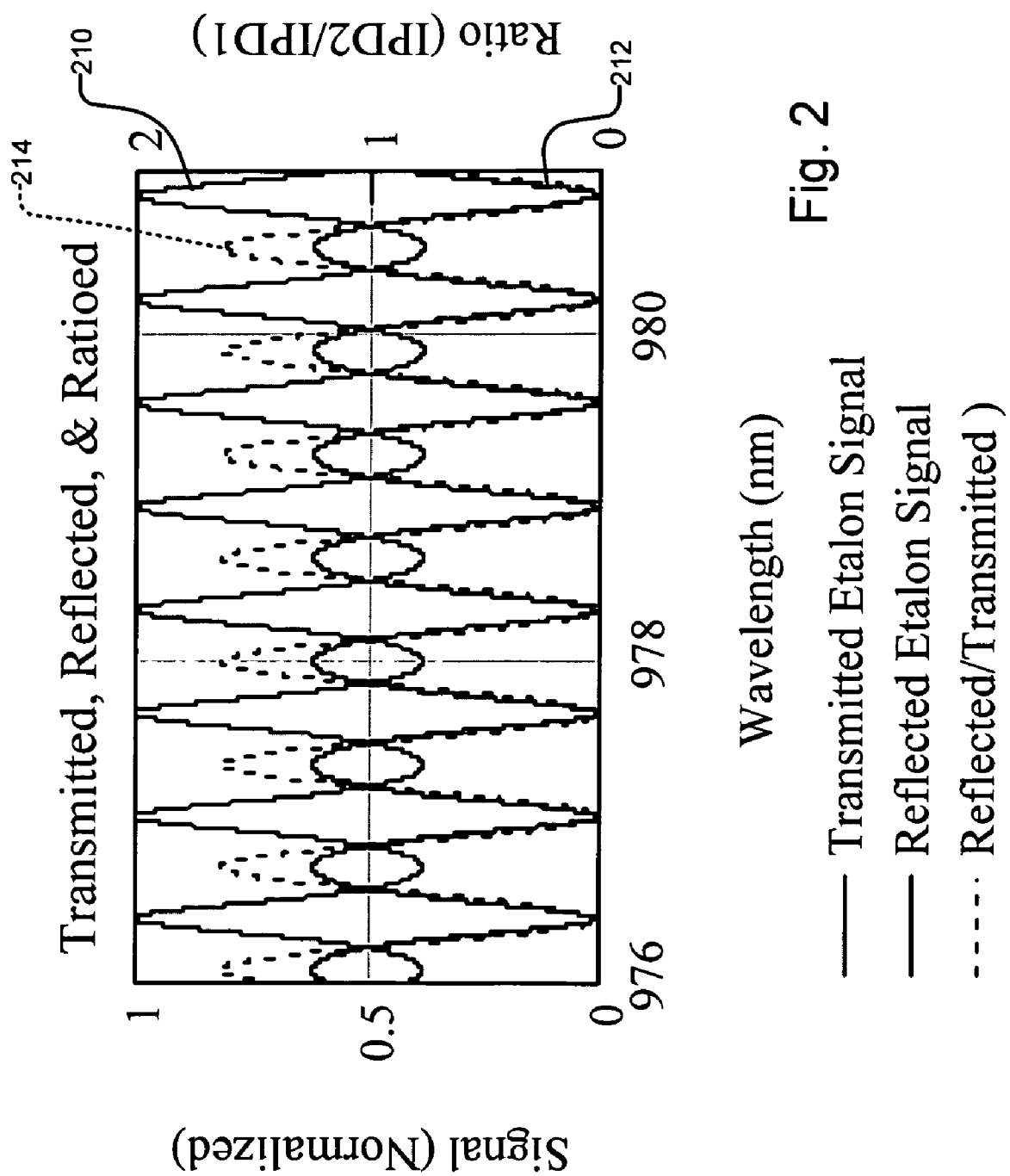
FIG. 2 is a plot of normalized signal as a function of wavelength illustrating the operation of the wavelength reference system according to the present invention.

FIG. 2 is a plot showing the relationship between the transmitted etalon signal reference element 134, the signal detected by photodetector pd1, see reference numeral 210, the reflective Etalon signal, specifically the signal detected by the diode pd2, reference numeral 212 and the reflective divided by transmitted signal 214, which is the division of these two responses formed by combining the response of pd1 and pd2.

Specifically, in the illustrated embodiment, the excitation signal 102 is scanned over a scan range of approximately 976 to 982 nanometers (nm) in one embodiment. In another embodiment, the range of 988 to 994 nm is used. The wavelength reference element etalon 134 has a free spectral range (FSR) of approximately 0.5 nanometers. As a result, the transmitted and reflective signals vary with a periodicity of approximately 0.5 nanometers over this range. From this information, both the amplitude of the excitation signal 102 and its wavelength can be determined according the following equations:

Incident Light $I_0$ is split with ~4% being sent to the Etalon and the rest discarded by partially reflective reference mirror 132.

Light Transmitted by the Etalon is sensed by Photodiode pd1, $I_{PD1}$.

96% of Light reflected by the etalon is sensed by Photodiode pd2, $I_{PD2}$.

The amplitude of I0 can be written as:

$$I_0 = K_1 \cdot (I_{PD1} + K_2 \cdot I_{PD2})$$

Wavelength is:

$$\lambda = f\left(\frac{I_{PD2}}{I_{PD1}}\right)$$

wherein $K_1$ and $K_2$ are experimentally determined constants.

Returning to FIG. 1, the excitation signal 102 that is not reflected by the partially reflective excitation mirror 122 passes through excitation optics. Specifically, the excitation optics comprise a focusing lens 124 and a diverging lens or concave lens 126. This has the effect of focusing the excitation signal down to a small diameter and increasing its working distance. Specifically, in the illustrated embodiment, a separation mirror device 128 is used. Specifically, this is a mirror that is angled relative to the axis of the excitation signal 102 and a collection axis 142 that passes through an input/output aperture 144 to the sample 20. The angled mirror 128 has a pinhole aperture 140 through which the excitation signal 102 passes to the output aperture 144. This configuration has advantages in easing alignment between the excitation and collection paths.

The sample 20, responding to the excitation signal 102 produces a Raman response. This is collected by a high numerical aperture (NA) system. Specifically, two focusing lenses 146 and 148 are used to collect the light from the sample 20 while improving the working distance. They are transmitted to a third focusing lens 150 that collimates the light from the sample 20. This light is then filtered by a first excitation filter 152 and a second excitation filter 154. Each of these filters stops or blocks the wavelengths in the scan band of the excitation signal 102. The two filters 152, 154 are used to fully suppress the response of the excitation signal 102 in the detected light. A fold mirror 156 is used to bend the light from the sample to a focusing lens 158 that couples the light into the spectroscopy subsystem 80.

The spectroscopy subsystem 80 detects and resolves the spectrum of the light returning from the sample 20. In the preferred embodiment, it comprises a spectrometer that resolves the spectrum of the sample light. Typically, these spectroscopy systems use gratings to disperse the spectrum over a detector array. In other examples, tunable filters are used along with single detector elements.

In the present embodiment, a combination of an etalon filter 82 and a grating 84 are used to produce a hybrid system. Specifically, preferred spectrometer configuration is as described in described in U.S. patent application Ser. No. 10/967,075, filed on Oct. 15, 2004 (US 2005-0264808 A1), which claims the benefit of U.S. Provisional Application Nos. 60/550,761, filed Mar. 5, 2004, and 60/512,146, filed Oct. 17, 2003, all of which are incorporated herein by this reference in their entirety. One or more lenses such as lenses 86 and 88 are used to collimate and relay the dispersed spectrum to the array detector 90.

The spectroscopy system controller 95 controls the power to the diode semiconductor chip 56 and the tuner 66 to thereby generate the tunable excitation signal 102 and scan this signal over the scan range, such as about 988 to 992 nanometers. Controller 95 further monitors the response of the first photodiode pd1 and the second photodiode pd2 in order to calculate both the wavelength and the amplitude of the excitation signal 102. With this information, including the response of the spectroscopy subsystem and specifically its detector array 90, the spectroscopy controller determines the Raman response of the sample 20.

In one example, the spectroscopy system controller 95 is implemented in electronics including possibly a field programmable gate array and a signal processor. This connects to a host computer 5, such as a standard personal computer. The spectroscopy system controller 95 loads the Raman spectral information to the host 5.

FIG. 3 is a scale perspective view of the probe system 100. Specifically, it illustrates the mechanical construction. Specifically, the probe 100 is manufactured in two parts. Specifically, a first substrate 302 is used to contain the optical elements associated with the excitation signal. Specifically, the collimating lens 112, the ASE filters 114, 116 and the polarizers 118, 120 are connected in the excitation portion 302. In the illustrated example, light traps such as 310 are provided to attenuate reflected light. The excitation substrate is connected to the signal collection substrate 304. Specifically, this allows different excitation and collection optics to be used by simply detaching the excitation substrate 302 from the collection substrate 304.

While this invention has been particularly shown and described with references to preferred embodiments thereof, it will be understood by those skilled in the art that various changes in form and details may be made therein without departing from the scope of the invention encompassed by the appended claims.

What is claimed is:

1. A probe subsystem for a Raman spectroscopy system, the probe subsystem comprising:
   a wavelength reference system that receives an excitation signal from a semiconductor source subsystem, the wavelength reference system determining a wavelength of the excitation signal, including:
      at least one reference detector for detecting a portion of the excitation signal prior to excitation of a sample to determine a wavelength of the excitation signal, and
      a wavelength reference element for filtering the excitation signal received by the at least one reference detector; and
   an output aperture through which the excitation signal is transmitted to the sample; and
   separation optics for enabling transmission of the excitation signal to the sample and receipt of a spectroscopic Raman response from the sample along a common axis extending through the output aperture.

2. A probe subsystem as claimed in claim 1, wherein the wavelength reference system further comprises:
   a second reference detector; and
   a partial reflector for dividing the excitation signal between the first reference detector and the second reference detector; and
   the wavelength reference element filtering the excitation signal received by the first reference detector and the second reference detector.

3. A probe subsystem as claimed in claim 2, further comprising a controller that uses the responses of the first reference detector and the second reference detector to determine the wavelength and a power of the excitation signal.

4. A probe subsystem as claimed in claim 1, further comprising a partially reflective mirror in a path of the excitation signal for tapping the portion of the excitation signal received by the wavelength reference system.

5. A probe subsystem as claimed in claim 4, further comprising excitation optics for shaping a beam of the semiconductor laser excitation signal after detection of the portion of the excitation signal by the wavelength reference system.

6. A probe subsystem as claimed in claim 1, wherein the separation optics comprises a mirror for reflecting light from the sample, the mirror comprising an optical port through which the excitation signal is transmitted to the sample.

7. A probe subsystem as claimed in claim 1, wherein the probe subsystem receives the excitation signal from a semiconductor tunable laser subsystem through an optical fiber.

8. A probe subsystem as claimed in claim 7, further comprising at least one amplified spontaneous emission filter for attenuating amplified spontaneous emission in the excitation signal after receipt from the optical fiber.

9. A probe subsystem as claimed in claim 7, further comprising at least one polarizer for improving a polarization of the excitation signal after receipt from the optical fiber.

10. A probe subsystem as claimed in claim 1, further comprising at least one polarizer for improving a polarization of the excitation signal.

11. A probe subsystem as claimed in claim 1, wherein the probe subsystem receives the excitation signal from a semiconductor tunable laser subsystem through a polarization maintaining optical fiber.

12. A Raman spectroscopy system, comprising:
    a tunable laser excitation subsystem comprising at least one tunable semiconductor diode for generating an excitation signal;
    a probe subsystem comprising:
       a wavelength reference system for determining a wavelength of the excitation signal comprising at least one reference detector for detecting a portion of the excitation signal prior to excitation of the sample and a wavelength reference element for filtering the excitation signal received by the reference detector; and
       an output aperture through which the excitation signal is transmitted to a sample; and
    a spectrometer subsystem for resolving a spectrum of light returning from the sample; and
    a controller for determining a Raman spectral response of the sample in response to the spectrum of light resolved by the spectrometer subsystem and the wavelength of the excitation signal from the wavelength reference system.

13. A system as claimed in claim 12, wherein the wavelength reference system comprises:
    a first reference detector for detecting a portion excitation signal prior to excitation of the sample;
    a second reference detector for detecting a portion excitation signal prior to excitation of the sample;
    a partial reflector for dividing the excitation signal between the first reference detector and the second reference detector; and
    a wavelength reference element for filtering the excitation signal received by the first reference detector and the second reference detector.

14. A system as claimed in claim 13, wherein the controller uses the responses of the first reference detector and the second reference detector to determine the wavelength and a power of the excitation signal.

15. A system as claimed in claim 12, wherein the probe subsystem comprises separation optics for enabling transmission of the excitation beam to the sample and receipt of the light from the sample along a common axis extending through the output aperture.

16. A system as claimed in claim 12, further comprising a fiber pigtail for transmitting the excitation signal from the semiconductor tunable laser subsystem to the probe subsystem.

17. A system as claimed in claim 12, wherein the probe subsystem comprises at least one polarizer for improving a polarization of the excitation signal.

18. A system as claimed in claim 12, further comprising polarization maintaining fiber for transmitting the excitation signal from the semiconductor tunable laser subsystem to the probe subsystem.

* * * * *